United States Patent [19]
Garland et al.

[11] Patent Number: 5,510,524
[45] Date of Patent: Apr. 23, 1996

[54] PROCESS FOR THE PRODUCTION OF A CARBOXYLIC ACID

[75] Inventors: Carl S. Garland, Silver Spring, Md.; Martin F. Giles, Middlesex, United Kingdom; Andrew D. Poole, Hampshire, United Kingdom; John G. Sunley, North Humberside, United Kingdom

[73] Assignee: BP Chemicals Limited, London, England

[21] Appl. No.: 458,692

[22] Filed: Jun. 2, 1995

[30] Foreign Application Priority Data

Feb. 21, 1995 [GB] United Kingdom ............ 9503384
Feb. 21, 1995 [GB] United Kingdom ............ 9503386

[51] Int. Cl.$^6$ ............ C07C 53/08; C07C 53/12; C07C 51/12
[52] U.S. Cl. ............ 562/519; 562/607; 562/522
[58] Field of Search ............ 562/519, 607, 562/522

[56] References Cited

U.S. PATENT DOCUMENTS

| | | |
|---|---|---|
| 3,769,329 | 10/1973 | Paulik et al. |
| 3,772,380 | 11/1973 | Paulik et al. |
| 4,746,640 | 5/1988 | Erpenbach et al. |
| 4,804,791 | 2/1989 | Kitson et al. ............ 568/885 |
| 4,918,226 | 4/1990 | Pruett ............ 562/607 |
| 4,985,572 | 7/1991 | Kitson et al. ............ 549/326 |
| 5,221,751 | 1/1994 | Schreck ............ 562/519 |

FOREIGN PATENT DOCUMENTS

| | | |
|---|---|---|
| 081152 | 6/1983 | European Pat. Off. |
| 0350635 | 1/1990 | European Pat. Off. |
| 0643034 | 3/1991 | European Pat. Off. |
| 0618184 | 10/1994 | European Pat. Off. |
| 3148006 | 6/1983 | Germany. |
| 51-065703 | 6/1976 | Japan. |
| 51-080813 | 7/1976 | Japan. |
| 57-081421 | 5/1982 | Japan. |
| 58-144347 | 8/1983 | Japan. |
| 58-167536 | 10/1983 | Japan. |
| 1234642 | 6/1971 | United Kingdom. |
| 1234641 | 6/1971 | United Kingdom. |
| 1276326 | 6/1972 | United Kingdom. |

OTHER PUBLICATIONS

P. Barret et al, "Reactivity of Solids": Proc. 10th International Symposium, J. Mol. Cat. 39 (1986) 137–138.
Brodski et al, J. Molec. Catalysis, 2 (1977) 149–14.
Smith et al, J. Molec. Catalysis, 39 (1987) 115–136.
Abel et al, J. Chem. Soc. 1958, pp. 3149–3152.

Primary Examiner—Arthur C. Prescott
Attorney, Agent, or Firm—Brooks Haidt Haffner & Delahunty

[57] ABSTRACT

A process for the production of a carboxylic acid by carbonylation of an alkyl alcohol or its reactive derivative comprises contacting the reactant with carbon monoxide in a liquid reaction composition comprising: (a) an iridium catalyst or rhodium catalyst, (b) alkyl halide, (c) at least a finite concentration of water and (d) rhenium as promoter.

13 Claims, 1 Drawing Sheet

Effect of rhenium addition at 22 barg total pressure.
○ Experiment H
● Example 8

PROCESS FOR THE PRODUCTION OF A CARBOXYLIC ACID

The present invention relates to a process for the production of a carboxylic acid by carbonylation of an alkyl alcohol and/or a reactive derivative thereof in the presence of an iridium catalyst or a rhodium catalyst.

Carbonylation processes in the presence of iridium catalysts are known and are described, for example, in U.S. Pat. No. 3772380, European patent publication number EP 0618184, UK patents GB 1276326, GB 1234641 and GB 1234642.

Carbonylation processes in the presence of rhodium catalysts are known and are described, for example, in U. S. Pat. No. 3769329.

Japanese laid-open patent application JP 51080813 to Mitsui Petrochemical Industries Ltd describes a method of producing carboxylic acids and/or esters thereof characterised in that alcohols and carbon monoxide are heated and reacted in the presence of a rhenium catalyst and halogen compounds.

J. Molecular Catalysis, 2(1977) 149–161 relates to iridium-catalysed homogenous carbonylation of methanol to acetic acid, using methyl iodide as promoter. Although it is stated that their studies with rhodium have shown a synergistic effect when a salt or a complex of zirconium, rhenium, cobalt or copper was used, the effect being most significant with copper, no experimental examples showing the promotional effect of any of these metals with rhodium are given.

It has now been found that rhenium has a beneficial effect on the rate of carbonylation of an alkyl alcohol and/or a reactive derivative thereof in the presence of an iridium catalyst or a rhodium catalyst particularly at low partial pressure of carbon monoxide and that rhenium can stabilise the catalyst, for example during separation of product from rhodium catalyst at reduced partial pressure of carbon monoxide. Thus, according to the present invention there is provided a process for the production of a carboxylic acid by carbonylation of an alkyl alcohol and/or a reactive derivative thereof which process comprises contacting said alcohol and/or a reactive derivative thereof with carbon monoxide in a liquid reaction composition in a carbonylation reactor; the liquid reaction composition comprising: (a) an iridium catalyst or a rhodium catalyst, (b) alkyl halide, (c) at least a finite concentration of water, and (d) rhenium as promoter.

Suitable alkyl alcohols comprise $C_1$ to $C_{10}$, preferably $C_1$ to $C_6$, more preferably $C_1$ to $C_4$ alkyl alcohols and yet more preferably methanol. Preferably, the alkyl alcohol is a primary or secondary alkyl alcohol. The carboxylic acid product of an alcohol having n carbon atoms is a carboxylic acid having n+1 carbon atoms.

Suitable reactive derivatives of the alkyl alcohol include the corresponding alkyl ester of the alcohol and the corresponding carboxylic acid product, dialkyl ethers and alkyl halides, preferably iodides or bromides. Suitable reactive derivatives of methanol include methyl acetate, dimethyl ether and methyl iodide. A mixture of alkyl alcohol and reactive derivatives thereof may be used as reactants in the process of the present invention. Preferably, methanol and/or methyl acetate are used as reactants. At least some of the alkyl alcohol and/or reactive derivative thereof will be converted to, and hence present as, alkyl ester in the liquid reaction composition by reaction with carboxylic acid product or solvent. When the catalyst is an iridium catalyst the concentration in the liquid reaction composition of alkyl ester is suitably in the range 1 to 70% by weight, preferably 2 to 50% by weight, more preferably 3 to 30% by weight.

When the catalyst is a rhodium catalyst the concentration in the liquid reaction composition, of alkyl ester is suitably in the range 0.1 to 50% by weight, preferably 0.5 to 50% by weight, more preferably 0.5 to 35% by weight. In a continuous process for the preparation of acetic acid by carbonylation of methanol in the presence of a rhodium catalyst the concentration of methyl aceatate in the liquid reaction composition may typically be up to 5% by weight.

Water may be formed in situ in the liquid reaction composition, for example, by the esterification reaction between alkyl alcohol reactant and carboxylic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Suitably, the concentration of water in the liquid reaction composition is in the range 0.1 to 15% by weight, preferably 1 to 15% by weight. Preferably, the concentration of water is maintained below 14%, more preferably below 11% and most preferably below 8% by weight.

The iridium catalyst in the liquid reaction composition may comprise any iridium containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 4H_2O$, $IrBr_3 4H_2O$, $Ir_3(CO)_{12}$, iridium metal, $Ir_2O_3$, $IrO_2$, $Ir(acac)(CO)_2$, $IR(acac)_3$, iridium acetate, $[Ir_3O(OAc)_6(H_2O)_3][OAc]$, and hexachloroiridic acid $[H_2IrCl_6]$, preferably, chloride- free complexes of iridium such as acetates, oxalates and acetoacetates which are soluble in one or more of the carbonylation reaction components such as water, alcohol and/or carboxylic acid. Particularly preferred is green iridium acetate which may be used in an acetic acid or aqueous acetic acid solution.

Preferably, the iridium catalyst concentration in the liquid reaction composition is in the range 100 to 6000 ppm by weight of iridium.

The rhodium catalyst in the liquid reaction composition may comprise any rhodium containing compound which is soluble in the liquid reaction composition. The rhodium catalyst may be added to the liquid reaction composition in any suitable form which dissolves in the liquid reaction composition or is convertible to a soluble form. Examples of suitable rhodium-containing compounds which may be added to the liquid reaction composition include $[Rh(CO)_2Cl]_2$, $[Rh(CO)_2I]_2$, $[Rh(Cod)cl]_2$, rhodium (III) chloride, rhodium (III) chloride trihydrate, rhodium (III) bromide, rhodium (III) iodide, rhodium (III) acetate, rhodium dicarbonylacetylacetonate, $RhCl_3(PPh_3)_3$ and $RhCl(CO)(PPh_3)_2$.

Preferably, the concentration of the rhodium catalyst in the liquid reaction composition is in the range from 1 ppm up to its limit of solubility in the reactor and/or product recovery system, typically 10 to 1500 ppm by weight of rhodium.

The rhenium promoter may comprise any rhenium containing compound which is soluble in the liquid reaction composition. The promoter may be added to the liquid reaction composition for the carbonylation reaction in any suitable form which dissolves in the liquid reaction composition or is convertible to soluble form.

Examples of suitable rhenium-containing compounds which may be used include $Re_2(CO)_{10}$, $Re(CO)_5Cl$, $Re(CO)_5Br$, $Re(CO)_5I$, $ReCl_3.xH_2O$, $ReCl_5.yH_2O$ and $[\{Re(CO)_4 I\}_2]$.

When the catalyst is an iridium catalyst, preferably, both the iridium- and rhenium-containing compounds are free of impurities which provide or generate in situ ionic iodides which may inhibit the reaction, for example, alkali or alkaline earth metal or other metal salts.

The molar ratio of rhenium promoter: iridium catalyst in the liquid reaction composition is suitably in the range 0.1:1 to 20:1, preferably in the range 0.1:1 to 10:1.

The molar ratio rhenium promoter: rhodium catalyst in the liquid reaction composition is suitably in the range 0.1:1 to 20:1, preferably in the range 1:1 to 10:1.

Suitable alkyl halides have alkyl moieties corresponding to the alkyl moiety of the alkyl alcohol reactant and are preferably $C_1$ to $C_{10}$, more preferably $C_1$ to $C_6$ and yet more preferably $C_1$ to $C_4$ alkyl halides. Preferably, the alkyl halide is an iodide or bromide, more preferably an iodide. Preferably, the concentration of alkyl halide in the liquid reaction composition is in the range 1 to 30%, preferably 1 to 20%, more preferably 2 to 16% by weight.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 bar partial pressure, as its presence may result in the formation of hydrogenation products. The partial pressure of carbon monoxide in the reactor is suitably in the range 1 to 70 bar, preferably 1 to 35 bar and more preferably 1 to 15 bar.

The total pressure in the carbonylation reactor is suitably in the range 10 to 200 barg, preferably 10 to 100 barg, more preferably 15 to 50 barg and yet more preferably 30 barg or less.

The promotional effect of rhenium in the catalyst systems of the present invention has been found to be most pronounced at relatively low partial pressure of carbon monoxide in the carbonylation reactor where the rate of reaction may be dependent upon the carbon monoxide partial pressure, for example for iridium-catalysed reactions at a partial pressure of less than or equal to 15 bar and for rhodium-catalysed reactions at a partial pressure of less than or equal to 7 bar. Under these conditions, it has been found that the catalyst system of the present invention has the advantage of providing an increased rate of reaction over catalyst systems without the rhenium promoter of the present invention. This advantage allows for increased rate of reaction under conditions when the carbon monoxide partial pressure is relatively low, for example due to a low total pressure in the carbonylation reactor or due to high vapour pressure of components of the liquid reaction composition, for example at high methyl acetate concentration in the liquid reaction composition or due to high concentration of inert gases (for example nitrogen and carbon dioxide) in the carbonylati on reactor. The catalyst system may also have advantages of increasing rate of carbonylation when the rate of reaction is reduced by the availability of carbon monoxide in solution in the liquid reaction composition resulting from mass transfer limitations, for example due to poor agitation.

The temperature of the carbonylation reaction is suitably in the range 100 to 300° C., preferably in the range 150°to 220° C., more preferably in the range 170°to 200° C.

Carboxylic acid may be used as a solvent for the reaction.

Ionic contaminants such as, for example, corrosion metals, particularly nickel, iron and chromium should be kept to a minimum in the liquid reaction composition when iridium is the catalyst as these may have an adverse effect on the reaction.

The process of the present invention may be performed as a batch or a continuous process, preferably as a continuous process.

The carboxylic acid product may be removed from the reactor by withdrawing liquid reaction composition and separating the carboxylic acid product by one or more flash and/or fractional distillation stages from the other components of the liquid reaction composition such as iridium or rhodium catalyst, rhenium promoter, alkyl halide, water and unconsumed reactants which may be recycled to the reactor to maintain their concentrations in the liquid reaction composition. The carboxylic acid product may be separated from the catalyst and promoter at a partial pressure of carbon monoxide less than that in the carbonylation reactor, for example at a partial pressure of 0.25 bar or less. The carboxylic acid product may also be removed as a vapour from the reactor.

The invention will now be illustrated by way of example only by reference to the following examples and by reference to FIG. 1 which shows in graph form the effect of rhenium on the rate of iridium-catalysed carbonylation of methanol at 22 barg total pressure.

Iridium-Catalysed Carbonylation Reactions

All experiments were performed using a 300 ml Hastelloy B2 (Trade Mark) autoclave equipped with a Dispersimax (Trade Mark) stirrer, liquid or solid catalyst injection facility and cooling coils. A gas supply to the autoclave was provided from a ballast vessel, feed gas being provided to maintain the autoclave at a constant pressure. The rate of gas uptake at a certain point in a reaction run was used to calculate the carbonylation rate, as number of moles of reactant consumed per litre of cold degassed reactor composition per hour (mol/l/hr), at a particular reactor composition (reactor composition based on a cold degassed volume).

The methyl acetate concentration was calculated during the course of the reaction from the starting composition, assuming that one mole of methyl acetate is consumed for every mole of carbon monoxide that is consumed. No allowance was made for organic components in the autoclave headspace.

When the liquid injection facility was used the autoclave was charged with the liquid components of the liquid reaction composition excluding part of the acetic acid and water charge in which the iridium catalyst ($H_2IrCl_6$) was dissolved.

When the solid catalyst injection facility was used the autoclave was charged with the liquid components of the liquid reaction composition while the catalyst ($IrCl_3$.hydrate) was charged to a small glass vial which was placed in the injection facility which injection facility was fitted to the underside of the lid of the autoclave.

If a promoter was used, this was placed in the autoclave, covered with a portion of the acetic acid charge (5 to 20 g), and the autoclave sealed. The autoclave was then pressure tested with nitrogen and vented via a gas sampling system. The autoclave was flushed with carbon monoxide several times (3×3–10 barg). The remaining liquid components of the reaction composition were then charged to the autoclave via a liquid addition port. The autoclave was then pressurised with carbon monoxide (typically 6 barg) and heated with stirring (1500 rpm) to reaction temperature. The total pressure was then raised to approximately 3 barg below the desired operating pressure by feeding carbon monoxide from the ballast vessel. Once stable at temperature (about 15 minutes) the catalyst was injected (from either the liquid or solid injection facility) using an over pressure of carbon monoxide. The reactor pressure was maintained constant (±0.5 barg) by feeding carbon monoxide gas from the ballast vessel throughout the course of the experiment. Gas uptake from the ballast vessel was measured using datalogging facilities throughout the course of the experiment. The reaction temperature was maintained within ±1° C. of the desired reaction temperature by means of a heating mantle connected to a Magus (Trade Mark) control system. In addition, excess heat of reaction was removed by means of cooling coils. At the end of the experiment the ballast vessel was isolated from the autoclave and the autoclave was crash cooled by means of the cooling coils. Gases in the head space of the autoclave were then sampled and analysed by gas chromatography. $IrCl_3$.hydrate and $H_2IrCl_6$ (22.2% w/w Ir aqueous solution) were supplied by Johnson Matthey.

Experiments A–D and Examples 1–5

The components of the reaction composition which were charged to the autoclave and to the liquid/solid injection facility for Experiments A–D and Examples 1–5 are shown in Table 1.

Reactions were performed using the procedure given above. The temperature and pressure at which Experiments A–D and Examples 1–5 were performed are given in Table 2 together with rate data at 26, 16 and 6% by weight calculated methyl acetate concentrations.

The results of the analyses of the non-condensable gases vented at the end of the experiments are given in Table 3.

Experiments A to D are not examples according to the present invention because no rhenium promoter was present in the liquid reaction composition.

Example 1 is an Example according to the present invention and demonstrates the benefit of about 4 molar equivalents of rhenium promoter to iridium catalyst on reaction rate at a reaction pressure of 20 barg and at a temperature of 195° C.

Example 2 is an Example according to the present invention and shows that at a reaction pressure of 20 barg and at a temperature of 190° C. the presence of about 2 molar equivalents of rhenium promoter to iridium catalyst has a beneficial effect on reaction rate. Example 3 is also an Example according to the present invention and demonstrates the benefit of an increase in the molar ratio of rhenium promoter to iridium catalyst on carbonylation rates.

Experiments E–I and Example 6–13

Further experiments were performed as above using a different autoclave but of the same capacity and construction as for previous experiments. Temperature control was by means of a Eurotherm (Trade Mark) controller. The experimental procedure was the same as before but only a liquid injection facility was used. In these experiments and examples it was determined that only 80% of the iridium catalyst solution was injected. The injection efficiency in the previous experiments was not determined.

The liquid reaction composition at the end of the experiment was analysed by gas chromatography.

The autoclave charges are given in Table 4, rate data in Table 5, by-products in Tables 6 and 7, and products of Experiment E and Example 12 in Table 8.

These experiments show the promotional effect of rhenium on an iridium-catalysed carbonylation process over a range of total reaction pressures. The results of the Experiments also show that under these conditions rhenium alone is not an effective carbonylation catalyst.

The data given in Table 8 show that in the absence of iridium (Experiment E) methyl acetate is recovered from the autoclave essentially unreacted, except for a small amount of methyl acetate which is hydrolysed to acetic acid and methanol under the reaction conditions. In agreement with this observation no carbon monoxide was observed to be taken up from the ballast vessel. In contrast, in the presence of both iridium and rhenium (Example 12) the major product is acetic acid.

BRIEF DESCRIPTION OF THE DRAWING

The carbonylation rates plotted against calculated methyl acetate concentration for Experiment H and Example 8 are shown in graph form in FIG. 1.

Comparison of Example 1 with Examples 4 and 5 shows that the promotional effect of rhenium on iridium-catalysed carbonylation is relatively greater at lower total pressure and hence lower partial pressure of carbon monoxide, but Example 7 shows that a promotional effect may be obtained at a total pressure in the carbonylation reactor at least as high as 28 barg. Similarly, compare Experiments F & G and Example 7 (28 barg) with Experiment K and Example 12 (19 barg).

TABLE 1

Figure 1:
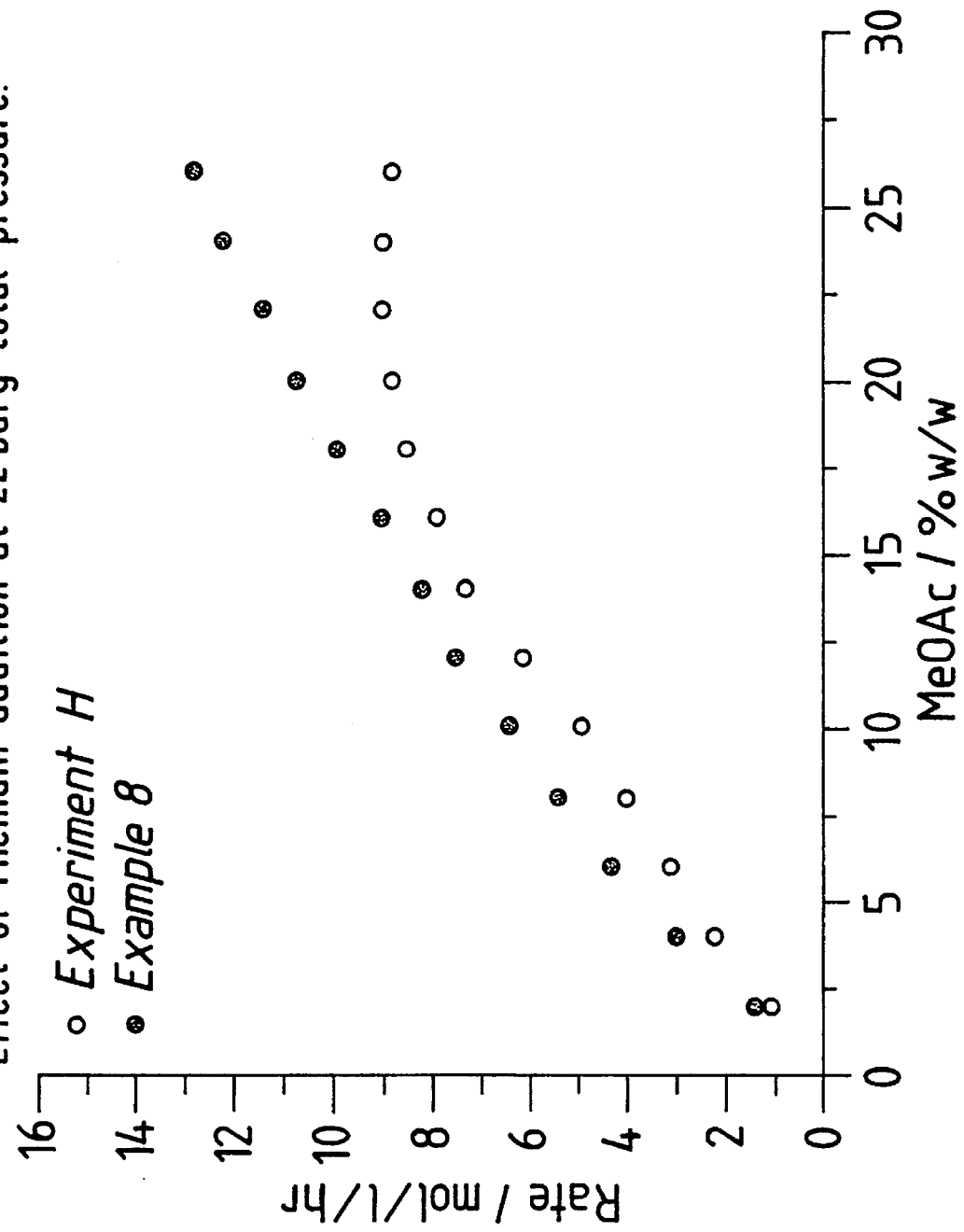

| | | | | | Autoclave charge. | | | | |
|---|---|---|---|---|---|---|---|---|---|
| Experiment | MeOAc (g) | AcOH (g) | MeI (g) | Water (g) | Promoter | Amount (g) | Catalyst | Amount (g) | Total charge (g) |
| Experiment A | 48.0 | 79.8 | 7.5 | 14.1 | — | — | $IrCl_3$.hydrate | 0.29 | 149.7 |
| Example 1 | 48.0 | 79.3 | 7.5 | 14.1 | $Re_2(CO)_{10}$ | 1.02 | $IrCl_3$.hydrate | 0.29 | 150.2 |
| Experiment B | 48.0 | 75.1 | 8.5 | 17.1 | — | — | $H_2IrCl_6$[a] | 1.51 | 150.2 |
| Experiment C | 48.0 | 75.1 | 8.5 | 17.1 | — | — | $H_2IrCl_6$ | 1.51 | 150.2 |
| Example 2 | 48.0 | 72.6 | 8.5 | 17.0 | $Re_2(CO)_{10}$ | 2.38 | $H_2IrCl_6$ | 1.51 | 150.0 |
| Example 3 | 47.8 | 64.8 | 12.7[b] | 17.0 | $Re_2(CO)_{10}$ | 4.76 | $H_2IrCl_6$ | 1.51 | 148.6 |
| Experiment D | 48.1 | 80.2 | 7.6 | 14.0 | — | — | $IrCl_3$.hydrate | 0.29 | 150.2 |
| Example 4 | 48.0 | 79.7 | 7.6 | 14.0 | $Re_2(CO)_{10}$ | 0.50 | $IrCl_3$.hydrate | 0.29 | 150.1 |
| Example 5 | 48.0 | 79.7 | 7.5 | 14.0 | $Re_2(CO)_{10}$ | 1.02 | $IrCl_3$.hydrate | 0.29 | 150.5 |

[a]Weight expressed as pure $H_2IrCl_6$
[b]Extra MeI added, 2 molar equivalents per mole of Re metal.

TABLE 2

Rate data

| Experiment | Pressure (barg) | Temp (°C.) | [Ir] (ppm) | Additive | Molar equivalents of metal to Ir | Rate (mol/l/hr) at 26% MeOAc concentration | Rate (mol/l/hr) at 16% MeOAc concentration | Rate (mol/l/hr) at 6% MeOAc concentration |
|---|---|---|---|---|---|---|---|---|
| Experiment A | 20 | 195 | 1050 | — | — | 5.0 | 4.2 | 1.7 |
| Example 1 | 20 | 195 | 1050 | Re | 4 | 7.4 | 5.2 | 2.5 |
| Experiment B | 20 | 190 | 4750 | — | — | 18.2 | 13.1 | 6.7 |
| Experiment C | 20 | 190 | 4750 | — | — | 17.1 | 12.5 | 6.9 |
| Example 2 | 20 | 190 | 4750 | Re | 2 | 18.7 | 14.2 | 8.3 |
| Example 3 | 20 | 190 | 4750 | Re | 4 | 21.7 | 15.7 | 7.9 |
| Experiment D[a] | 28 | 195 | 1050 | — | — | 11.0 | 7.6 | 3.4 |
| Example 4[a] | 28 | 195 | 1050 | Re | 2 | 10.9 | 7.6 | 2.8 |
| Example 5[a] | 28 | 195 | 1050 | Re | 4 | 11.3 | 7.7 | 3.3 |

[a]Mean of two identical experiments.

TABLE 3

Gaseous by-products

| Experiment | Pressure (barg) | Additive | Molar equivalents of metal to Ir | Hydrogen (% v/v) | $CO_2$ (% v/v) | Methane (% v/v) |
|---|---|---|---|---|---|---|
| Experiment A | 20 | — | — | 1.2 | 1.5 | 4.1 |
| Example 1 | 20 | Re | 4 | 1.3 | 2.1 | 5.5 |
| Experiment B | 20 | — | — | — | — | — |
| Experiment C | 20 | — | — | 1.1 | 2.6 | 6.7 |
| Example 2 | 20 | Re | 2 | 1.6 | 3.1 | 10.0 |
| Example 3 | 20 | Re | 4 | 1.4 | 4.5 | 10.2 |
| Experiment D | 28 | — | — | 1.7 | 1.8 | 3.8 |
| Example 4[a] | 28 | Re | 2 | 2.5 | 1.8 | 3.7 |
| Example 5[a] | 28 | Re | 4 | 2.2 | 4.4 | 3.7 |

[a]Mean of two identical experiments.
[b]All reactions conducted for a period of 1 hour. Analysis is of cold (ambient temp.) vented off-gas.

TABLE 4

Autoclave charge.

| Experiment | MeOAc (g) | AcOH (g) | MeI (g) | Water (g) | Additive | Amount (g) | Catalyst | Catalyst (g)[a] | Total charge (g) |
|---|---|---|---|---|---|---|---|---|---|
| E | 48.0 | 76.6 | 6.3 | 17.0 | $Re_2(CO)_{10}$ | 2.05 | — | — | 150.0 |
| F | 48.0 | 77.1 | 7.4 | 17.0 | — | — | $H_2IrCl_6$ | 0.65 | 150.2 |
| G | 48.0 | 77.1 | 7.3 | 17.0 | — | — | $H_2IrCl_6$ | 0.64 | 150.0 |
| 6 | 48.0 | 76.2 | 7.4 | 17.0 | $Re_2(CO)_{10}$ | 1.03 | $H_2IrCl_6$ | 0.65 | 150.3 |
| 7 | 48.0 | 75.0 | 7.3 | 17.0 | $Re_2(CO)_{10}$ | 2.04 | $H_2IrCl_6$ | 0.65 | 150.0 |
| H | 48.0 | 76.9 | 8.6 | 16.1 | — | — | $H_2IrCl_6$ | 0.64 | 150.2 |
| I | 48.0 | 77.1 | 7.4 | 17.1 | — | — | $H_2IrCl_6$ | 0.65 | 150.3 |
| 8 | 48.0 | 75.1 | 7.3 | 17.1 | $Re_2(CO)_{10}$ | 2.05 | $H_2IrCl_6$ | 0.65 | 150.2 |
| K | 48.0 | 77.1 | 7.4 | 17.0 | — | — | $H_2IrCl_6$ | 0.65 | 150.2 |
| 9 | 48.0 | 76.9 | 7.3 | 17.0 | $Re_2(CO)_{10}$ | 0.51 | $H_2IrCl_6$ | 0.64 | 150.4 |
| 10 | 48.1 | 76.1 | 7.4 | 17.0 | $Re_2(CO)_{10}$ | 1.03 | $H_2IrCl_6$ | 0.64 | 150.3 |
| 11 | 48.1 | 76.0 | 7.3 | 17.0 | $Re_2(CO)_{10}$ | 1.03 | $H_2IrCl_6$ | 0.65 | 150.1 |
| 12 | 48.0 | 75.0 | 7.5 | 17.0 | $Re_2(CO)_{10}$ | 2.05 | $H_2IrCl_6$ | 0.64 | 150.2 |
| 13 | 48.2 | 74.8 | 7.3 | 17.0 | $Re(CO)_5Cl$ | 2.25 | $H_2IrCl_6$ | 0.64 | 150.2 |

[a]Weight expressed as pure $H_2IrCl_6$.

TABLE 5

Rate data[a]

| Experiment | Pressure (barg) | Temp (°C.) | Additive | [Re] (ppm) | Rate (mol/l/hr) at 26% MeOAc concentration | Rate (mol/l/hr) at 16% MeOAc concentration | Rate (mol/l/hr) at 6% MeOAc concentration |
|---|---|---|---|---|---|---|---|
| E | 28 | 190 | $Re_2(CO)_{10}$ | 7800 | — | — | — |
| F | 28 | 190 | — | — | 12.4 | 9.2 | 3.8 |
| G | 28 | 190 | — | — | 11.8 | 9.3 | 4.0 |
| 6 | 28 | 190 | $Re_2(CO)_{10}$ | 3900 | 12.0 | 9.8 | 4.3 |
| 7 | 28 | 190 | $Re_2(CO)_{10}$ | 7800 | 15.2 | 11.4 | 5.0 |
| H | 22 | 190 | — | — | 8.8 | 7.9 | 3.1 |
| I | 22 | 190 | — | — | 8.7 | 7.5 | 3.2 |
| 8 | 22 | 190 | $Re_2(CO)_{10}$ | 7800 | 12.8 | 9.0 | 4.3 |
| K | 19 | 190 | — | — | 7.9 | 6.5 | 2.8 |
| 9 | 19 | 190 | $Re_2(CO)_{10}$ | 1900 | 8.5 | 7.0 | 2.9 |
| 10 | 19 | 190 | $Re_2(CO)_{10}$ | 3900 | 10.1 | 8.3 | 3.9 |
| 11 | 19 | 190 | $Re_2(CO)_{10}$ | 3900 | 10.3 | 7.6 | 3.2 |
| 12 | 19 | 190 | $Re_2(CO)_{10}$ | 7800 | 10.8 | 9.1 | 3.9 |
| 13 | 19 | 190 | $Re(CO)_5Cl$ | 7700 | 9.4 | 7.9 | 3.4 |

[a]Iridium concentration 1600 ppm at t = 0 based upon a catalyst inject efficiency of 80%. Stirrer speed 1500 rpm.

TABLE 6

Gaseous by-products[a]

| Experiment | Pressure (barg) | Additive | [Re] (ppm) | Reaction time (minutes) | Hydrogen (mmol) | $CO_2$ (mmol) | Methane (mmol) |
|---|---|---|---|---|---|---|---|
| E | 28 | $Re_2(CO)_{10}$ | 7800 | 38 | 3.1 | 0.3 | 0.3 |
| F | 28 | — | — | 39 | 5.9 | 5.2 | 5.5 |
| G | 28 | — | — | 57 | 5.6 | 4.9 | 6.7 |
| 6 | 28 | $Re_2(CO)_{10}$ | 3900 | 38 | 6.2 | 5.1 | 6.9 |
| 7 | 28 | $Re_2(CO)_{10}$ | 7800 | 39 | 7.0 | 7.0 | 10.6 |
| H | 22 | — | — | 58 | 4.3 | 6.0 | 9.7 |
| I | 22 | — | — | 48 | 4.0 | 5.7 | 11.4 |
| 8 | 22 | $Re_2(CO)_{10}$ | 7800 | 39 | 4.8 | 5.4 | 11.1 |

[a]Analysis is of cold (ambient temperature) vented off-gas.

TABLE 7

Liquid by-products[a]

| Experiment | Pressure (barg) | Additive | [Re] (ppm) | Reaction time (minutes) | EtOAc (ppm) | EtI (ppm) | Propionic acid (ppm) |
|---|---|---|---|---|---|---|---|
| E | 28 | $Re_2(CO)_{10}$ | 7800 | 38 | 10 | 47 | 5 |
| F | 28 | — | — | 39 | 215 | 207 | 12 |
| G | 28 | — | — | 57 | 196 | 333 | 14 |
| 6 | 28 | $Re_2(CO)_{10}$ | 3900 | 38 | 230 | 189 | 14 |
| 7 | 28 | $Re_2(CO)_{10}$ | 7800 | 39 | 273 | 381 | 75 |
| H | 22 | — | — | 58 | 207 | 240 | 55 |
| I | 22 | — | — | 48 | 198 | 165 | 84 |
| 8 | 22 | $Re_2(CO)_{10}$ | 7800 | 39 | 266 | 181 | 20 |
| K | 19 | — | — | 63 | 218 | 238 | 15 |
| 9 | 19 | $Re_2(CO)_{10}$ | 1900 | 56 | 198 | 161 | 50 |
| 10 | 19 | $Re_2(CO)_{10}$ | 3900 | 47 | 244 | 198 | 16 |
| 11 | 19 | $Re_2(CO)_{10}$ | 3900 | 57 | 291 | 359 | 88 |
| 12 | 19 | $Re_2(CO)_{10}$ | 7800 | 47 | 263 | 237 | 17 |
| 13 | 19 | $Re(CO)_5Cl$ | 7700 | 47 | 148 | 198 | 10 |

[a]Trace levels, typically < 2 ppm, of acetaldehyde were also found except for Experiment E which contained 50 ppm acetaldehyde.

TABLE 8

Analysis of final liquid reaction composition

| Experiment | Acetic acid (% w/w) | Methyl Iodide (% w/w) | Methyl acetate (% w/w) | Methanol (% w/w) |
|---|---|---|---|---|
| Experiment E | 54.7 | 3.3 | 28.3 | 1.3 |
| Example 12 | 90.3 | 2.7 | 1.3 | — |

Rhodium-Catalysed Carbonylations

A 150 ml Hastelloy B2 (Trade Mark) autoclave equipped with a Magnedrive (Trade Mark) stirrer, liquid injection facility and cooling coils was used for a series of batch carbonylation experiments. A gas supply to the autoclave was provided from a gas ballast vessel, feed gas being provided to maintain the autoclave at a constant pressure. The rate of gas uptake was calculated (with an accuracy believed to be ±/-1%) from the rate at which the pressure falls in the gas ballast vessel.

For each batch carbonylation experiment the autoclave was charged with the rhenium promoter where appropriate and the liquid components of the liquid reaction composition excluding part of the acetic acid charge, in which the rhodium catalyst was dissolved.

The autoclave was flushed twice with nitrogen (28 barg), and was then heated with stirring (1000 rpm) to 185° C. On attaining a temperature of 185 ° C. nitrogen was introduced into the autoclave to achieve a desired pressure, which pressure was less than the final reaction pressure. The gas feed lines to the autoclave were then vented free of nitrogen and were filled with carbon monoxide. After allowing the system to stabilise for about 30 minutes, the rhodium catalyst in acetic acid solution, or acetic acid and methyl acetate solution, was then injected into the autoclave under pressure of carbon monoxide. The autoclave was subsequently maintained at a desired pressure in the range 27 to 28 barg by feeding carbon monoxide gas on demand from the gas ballast vessel through the liquid injection facility. The partial pressure of carbon monoxide employed in the experiment was calculated by subtracting the observed pressure when nitrogen was first introduced to the autoclave from the final reaction pressure.

Gas uptake from the ballast vessel was measured every 30 seconds and from this was calculated the rate of carbonylation, expressed as moles of carbon monoxide consumed per litre of cold degassed liquid reaction composition per hour (mol/l/hr). In the examples the concentrations of components such as methyl acetate and water in the reaction composition during the carbonylation reaction may be calculated from the starting composition assuming that one mole of reactant is consumed for every mole of carbon monoxide that is consumed. After tiptake of carbon monoxide from the ballast vessel had ceased or the period of the reaction had proceeded for 40 minutes, whichever was sooner, the autoclave was isolated from the gas supply. The autoclave as subsequently cooled to room temperature and the gases were cautiously vented from the autoclave and analysed by gas chromatography. The liquid reaction composition was then discharged from the autoclave, sampled and was analysed by gas chromatography for liquid products and by-products.

To obtain a reliable baseline a number of identical baseline runs may have to be performed to condition the autoclave such that consistent rates are achieved. This conditioning period is often different from autoclave to autoclave and may depend upon its previous history.

Experiments L–N and Example 14

The components of the reaction composition which were charged to the autoclave and to the liquid injection facility for Experiments L–N and Example 14 are shown in Table 9.

Reactions were performed using the procedure given above. The temperature and pressure at which Experiments L–N and Example 14 were performed are given in Table 10 together with the carbon monoxide partial pressure and carbonylation rate data after a reaction time of 5 minutes.

The results of the analyses of the vented gases at the end of the experiments are given in Table 11. In all the experiments acetic acid was the major product (selectivity 99% by weight).

Experiments L and M are not examples according to the present invention because no rhenium promoter was present in the liquid reaction composition. In both Experiments L and M there was evidence of significant catalyst precipitation when the autoclave was opened at the end of the experiment.

Experiment N is not an example according to the present invention because no rhodium catalyst was present in the liquid reaction composition. In this experiment nitrogen was not introduced to the autoclave on attaining a temperature of 185° C. and before carbon monoxide was fed to the autoclave. Thus, the partial pressure of carbon monoxide was higher than in Experiments L and M. This experiment showed that even under a relatively high partial pressure of carbon monoxide, rhenium alone did not act as a carbonylation catalyst.

Example 14 is an example according to the present invention because both rhenium promoter and rhodium catalyst were present in the liquid reaction composition. There was little evidence of catalyst precipitation on opening the autoclave at the end of the experiment. This example demonstrates that addition of rhenium promoter to the liquid reaction composition affords the benefits of improved catalyst stability and increase in carbonylation rate. The improved catalyst stability demonstrated in Example 14 will be particularly beneficial during separation of the carboxylic acid product from the catalyst during product recovery stages in which carbon monoxide partial pressure is less than that in the carbonylation reaction.

TABLE 9

| | Autoclave charge. | | | | | | | |
|---|---|---|---|---|---|---|---|---|
| Experiment | MeOAc (mmol) | AcOH (mmol)[a] | MeI (mmol) | Water (mmol) | Promoter | Amount (mmol) | Catalyst | Catalyst (mmol)[b] |
| Experiment L | 244 | 704 | 101 | 911 | — | — | $Rh_2(CO)_4Cl_2$ | 0.20 |
| Experiment M | 244 | 703 | 102 | 911 | — | — | $Rh_2(CO)_4Cl_2$ | 0.20 |
| Experiment N | 244 | 786 | 102 | 911 | $Re_2(CO)_{10}$ | 1.98 | — | — |
| Example 14 | 244 | 702 | 102 | 912 | $Re_2(CO)_{10}$ | 1.97 | $Rh_2(CO)_4Cl_2$ | 0.20 |

[a] charged to the autoclave at the start of the experiment
[b] dissolved in acetic acid (83 mmol)

TABLE 10

| Experiment | Pressure (barg) | Partial Pressure of Carbon Monoxide (barg) at start of reaction | Temp (°C.) | Rate data[a] Rate (mol/l/hr) after 5 minutes | Rate (mol/l/hr) at 18% w/w calculated Methyl Concentration In Reaction Composition | Carbon monoxide consumed (mmol) | % MeOAc consumed[a] |
|---|---|---|---|---|---|---|---|
| Experiment L | 27.5 | 4.8 | 185 | 3.6 | 3.4 | 104[b] | 43 |
| Experiment M | 27.3 | 4.3 | 185 | 2.4 | 2.1 | 56[b] | 23 |
| Experiment N | 28.0[d] | unknown | 185 | 0 | 0 | 0[c] | 0 |
| Example 14 | 27.4 | 4.4 | 185 | 4.5 | 4.6 | 199[c] | 82 |

[a]based on carbon monoxide gas uptake data.
[b]after reaction ceased.
[c]reaction was stopped after 40 minutes.
[d]on attaining a temperature of 185° C. the system was allowed to stabilise for about 30 minutes before the autoclave was pressurised with carbon monoxide gas only.

TABLE 11

| | By-products | |
|---|---|---|
| | Gaseous By-products[a] (% v/v) | |
| Experiment | $CO_2$ | Methane |
| Experiment L | 4.3 | 9.5 |
| Experiment M | 4.0 | 9.3 |
| Experiment N | trace | 1.3 |
| Example 14 | 3.5 | 10.9 |

[a]Compositions expressed as % by volume of measurable gas including balance of nitrogen and carbon monoxide but excluding hydrogen which is not measurable by this analysis.

We claim:

1. A process for the production of a carboxylic acid by carbonylation of an alkyl alcohol and/or a reactive derivative thereof which process comprises contacting said alcohol and/or a reactive derivative thereof with carbon monoxide in a liquid reaction composition in a carbonylation reactor; the liquid reaction composition comprising: (a) an iridium catalyst or a rhodium catalyst, (b) alkyl halide, (c) at least a finite concentration of water, and (d) rhenium as promoter.

2. A process as claimed in claim 1 in which the molar ratio of rhenium:iridium catalyst in the liquid reaction composition is in the range 0.1:1 to 20:1, preferably in the range 0.1:1 to 10:1.

3. A process as claimed in claim 2 in which the total pressure in said carbonylation reactor is 30 barg or less.

4. A process as claimed in claim 2 in which the partial pressure of carbon monoxide in said carbonylation reactor in less than or equal to 15 bar.

5. A process as claimed in claim 2, claim 3 or claim 4 in which the liquid reaction composition further comprises alkyl ester in the range 1 to 70% by weight, preferably 2 to 50% by weight, more preferably 3 to 30% by weight.

6. A process as claimed in claim 5 in which the carboxylic acid product comprises acetic acid and the alkyl ester comprises methyl acetate.

7. A process as claimed in claim 1 in which the molar ratio of rhenium:rhodium catalyst in the liquid reaction composition is in the range 0.1:1 to 20:1, preferably in the range 1:1 to 10:1.

8. A process as claimed in claim 7 in which the liquid reaction composition further comprises alkyl ester in the range 0.1 to 50% by weight, preferably 0.5 to 50% by weight, more preferably 0.5 to 35% by weight.

9. A process as claimed in claim 8 in which the carboxylic and product comprises acetic acid and the alkyl ester comprises methyl acetate.

10. A process as claimed in claim 9 in which the concentration of methyl acetate is up to 5% by weight.

11. A process as claimed in any one of claims 7 to 10 in which the partial pressure of carbon monoxide in said carbonylation reactor is less than or equal to 7 bar.

12. A process as claimed in any one of claims 1, 7, 8, 9 and 10 in which the carboxylic acid product is separated from the catalyst at a carbon monoxide partial pressure less than that in the carbonylation reactor.

13. A process as claimed in claim 11 in which the carboxylic and product is separated from the catalyst at a carbon monoxide partial pressure less than that in the carbonylation reactor.

* * * * *

UNITED STATES PATENT AND TRADEMARK OFFICE
CERTIFICATE OF CORRECTION

PATENT NO. : 5,510,524
DATED : April 23, 1996
INVENTOR(S) : Carl S. Garland, Martin F. Giles, Andrew D. Poole and John G. Sunley It is certified that error appears in the above-indentified patent and that said Letters Patent is hereby corrected as shown below:

Col. 1, l. 37, "Thus, according to" should start a new paragraph

Col. 2, l. 34, should read "Ir(acac)$_3$,"

Col. 2, l. 52, should read "[Rh(Cod)$\underline{C}$l]$_2$,"

Col. 2, l. 55, should read "RhCl$_3$(PPh$_3$)$_3$"

Col. 3, l. 17, correct the spelling of the word "mo$\underline{i}$eties"

Col. 5, l. 19, "IrCl$_3$, hydrate" should start a new paragraph

Col. 11, l. 9, should read "be +/-1%"

Col. 11, l. 41, correct the spelling of the word "uptake"

Col. 12, l. 20, should read ".(selectivity $>$ 99%"

Signed and Sealed this

Fifteenth Day of October, 1996

Attest:

BRUCE LEHMAN

*Attesting Officer*   *Commissioner of Patents and Trademarks*